(12) United States Patent
Blalock et al.

(10) Patent No.: US 8,199,329 B2
(45) Date of Patent: *Jun. 12, 2012

(54) APPARATUS FOR MEASUREMENT OF THE AXIAL LENGTH OF AN EYE

(75) Inventors: Todd F. Blalock, Penfield, NY (US); Filipp V. Ignatovich, Rochester, NY (US)

(73) Assignee: Lumetrics, Inc, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/980,110

(22) Filed: Dec. 28, 2010

(65) Prior Publication Data

US 2011/0090461 A1    Apr. 21, 2011

Related U.S. Application Data

(63) Continuation of application No. 12/150,486, filed on Apr. 28, 2008, now Pat. No. 7,884,946.

(51) Int. Cl.
*G01B 11/02* (2006.01)
(52) U.S. Cl. ...................................................... 356/497
(58) Field of Classification Search .................. 356/477, 356/479, 497, 491, 492, 505
See application file for complete search history.

(56) References Cited

U.S. PATENT DOCUMENTS

| | | | |
|---|---|---|---|
| 4,681,445 A | | 7/1987 | Perkins |
| 5,347,328 A | | 9/1994 | Sekine et al. |
| 5,596,409 A | | 1/1997 | Marcus et al. |
| 5,975,697 A | * | 11/1999 | Podoleanu et al. ............ 351/206 |
| 6,002,480 A | * | 12/1999 | Izatt et al. ...................... 356/479 |
| 6,006,128 A | * | 12/1999 | Izatt et al. ...................... 600/476 |
| 6,201,608 B1 | | 3/2001 | Mandella et al. |
| 6,243,191 B1 | | 6/2001 | Fercher |
| 6,307,634 B2 | | 10/2001 | Hitzenberger et al. |
| 6,421,164 B2 | | 7/2002 | Tearney et al. |
| 6,735,463 B2 | * | 5/2004 | Izatt et al. ...................... 600/476 |
| 7,006,232 B2 | * | 2/2006 | Rollins et al. .................. 356/479 |
| 7,075,658 B2 | * | 7/2006 | Izatt et al. ...................... 356/479 |
| 7,242,480 B2 | | 7/2007 | Alphonse |
| 7,307,733 B2 | * | 12/2007 | Chan et al. ..................... 356/489 |
| 7,312,876 B2 | * | 12/2007 | Chan et al. ..................... 356/487 |
| 7,331,669 B2 | * | 2/2008 | Elsner ............................ 351/206 |
| 7,372,578 B2 | * | 5/2008 | Akiba et al. ................... 356/495 |
| 7,400,410 B2 | * | 7/2008 | Baker et al. .................... 356/498 |
| 7,408,648 B2 | * | 8/2008 | Kleen et al. .................... 356/479 |
| 7,428,086 B2 | | 9/2008 | Dufour et al. |
| 7,434,932 B2 | * | 10/2008 | Hanebuchi ..................... 351/206 |

(Continued)

OTHER PUBLICATIONS

Stenstrom, Solve, "Investigation of the Variation and the Correlation of the Optical Elements of Human Eyes" American Journal of Optometry and Archives of American Academy of Optometry, Columbia University Optometry Laboratory, New York, New York, Jul. 1948, vol. 25., No. 7, pp. 341-351.

(Continued)

*Primary Examiner* — Tarifur Chowdhury
*Assistant Examiner* — Jonathan Hansen
(74) *Attorney, Agent, or Firm* — Patent Innovations LLC; John M. Hammond

(57) ABSTRACT

An apparatus for measuring the axial length of a human eye, the apparatus comprising a low coherence light source; a beam splitter; a fast displacement module for rapidly varying the path length within a reference arm of an interferometer; a laser directing a laser beam that is co-propagating with light from the low coherence light source into the displacement module.

5 Claims, 4 Drawing Sheets

U.S. PATENT DOCUMENTS

| | | | |
|---|---|---|---|
| 7,480,059 B2 * | 1/2009 | Zhou et al. | 356/498 |
| 7,492,466 B2 * | 2/2009 | Chan et al. | 356/497 |
| 7,884,946 B2 * | 2/2011 | Blalock et al. | 356/497 |
| 2005/0213103 A1 | 9/2005 | Everett et al. | |
| 2006/0055939 A1 | 3/2006 | Akiba et al. | |
| 2006/0100490 A1 | 5/2006 | Wang et al. | |
| 2007/0076217 A1 | 4/2007 | Baker et al. | |
| 2007/0236700 A1 | 10/2007 | Yun et al. | |
| 2008/0065710 A1 | 3/2008 | Fiorentino et al. | |
| 2008/0180683 A1 | 7/2008 | Kemp | |
| 2008/0267562 A1 | 10/2008 | Wang et al. | |
| 2009/0207418 A1 | 8/2009 | Kim et al. | |

OTHER PUBLICATIONS

Office Action of Jul. 19, 2010 of parent U.S. Appl. No. 12/150,486, now U.S. Patent No. 7,884,946.

* cited by examiner

APPARATUS FOR MEASUREMENT OF THE AXIAL LENGTH OF AN EYE

CROSS-REFERENCE TO RELATED PATENT APPLICATIONS

This application is a continuation of copending U.S. patent application Ser. No. 12/150,486, filed on Apr. 28, 2008, the disclosure of which is incorporated herein by reference.

This invention relates in one embodiment to an apparatus for measuring the axial length of a human eye, and more particularly to an interferometric apparatus that operates with high precision and high speed.

BACKGROUND

1. Field of the Invention

Interferometric systems for measuring the axial length of the human eye.

2. Description of Related Art

Low-coherence interferometry (LCI) is a powerful non-contact measurement technique. It is used to interferometrically measure and characterize weak scattering signals using low-coherence light. It finds broad use in microscopy, sensing applications for quality control in semiconductor and other industries, and for medical applications such as Optical Coherence Tomography (OCT). Measurement systems using the principles of low-coherence interferometry are sold commercially. For example, the OPTIGAGE™ that is manufactured and sold by Lumetrics. Inc. of West Henrietta N.Y., is based on LCI and may be used to measure thicknesses of various multilayered materials, such as lens stacks, auto glass, polymer films, medical tubing and other objects.

There are generally two main approaches used in low-coherence interferometry: Spectral Domain Interferometry (SDI), and Time Domain (TDI) Interferometry. The two approaches are different in speed, sensitivity, and measurement range. SDI has superior sensitivity and speed; however, it also has small measurement range. It is mainly used in optical coherence tomography, which requires image acquisitions at video-rates (on the order of 30 frames per second), and in general, does not involve large measurement ranges. TDI has a virtually unlimited dynamic range. However it is generally less sensitive and is much slower than SDI.

Non-invasive measurements of the axial eye length require large measurement range and thus cannot be achieved using SDI. While the TDI sensitivity is sufficient to detect the light reflected by the ocular interfaces, its speed is not sufficient to perform the axial length measurement of an eye. In general, it is difficult for a human subject to hold his eyes motionless for more than about 100 milliseconds. Thus the measurement should be made at a rate greater than 10 Hz, and preferably at least about 15 Hz.

Additionally, increased measurement speed is also associated with reduced sensitivity, which cannot be improved by simply increasing the output power of the light source, as the amount of the incident light is limited by safety regulations. The light source cannot be so powerful as to cause damage to the eye during a measurement cycle.

Accordingly, there remains a need for an inexpensive and robust method for measuring the axial length of a human eye, which has sufficient sensitivity to perform the length measurements with high speed and high precision.

SUMMARY

The present invention meets this need by providing an apparatus for measuring the axial length of an eye, the apparatus comprising a low coherence light source; a beam splitter; a fast displacement module for rapidly varying the path length within a reference arm of an interferometer; a laser directing a laser beam that is co-propagating with light from the low coherence light source into the displacement module. An apparatus according to the invention may also include an optical probe comprised of a first polarizing beam splitter and a second polarizing beam splitter positioned to provide two polarized beams having differing path lengths.

If the variation in path length caused by the fast displacement module is greater than the optical length of the eye, it is possible to measure the entire eye without the use of the beam splitter. If the variation in path length caused by the beam splitter is less than the optical length of the eye (as in FIG. 3), the beam splitters can be used to displace the measuring segments along the entire length of the eye (or selected portions of it) to obtain the described measurements.

BRIEF DESCRIPTION OF THE DRAWINGS

The invention will be described by reference to the following drawings, in which like numerals refer to like elements, and in which.

Figure 1:
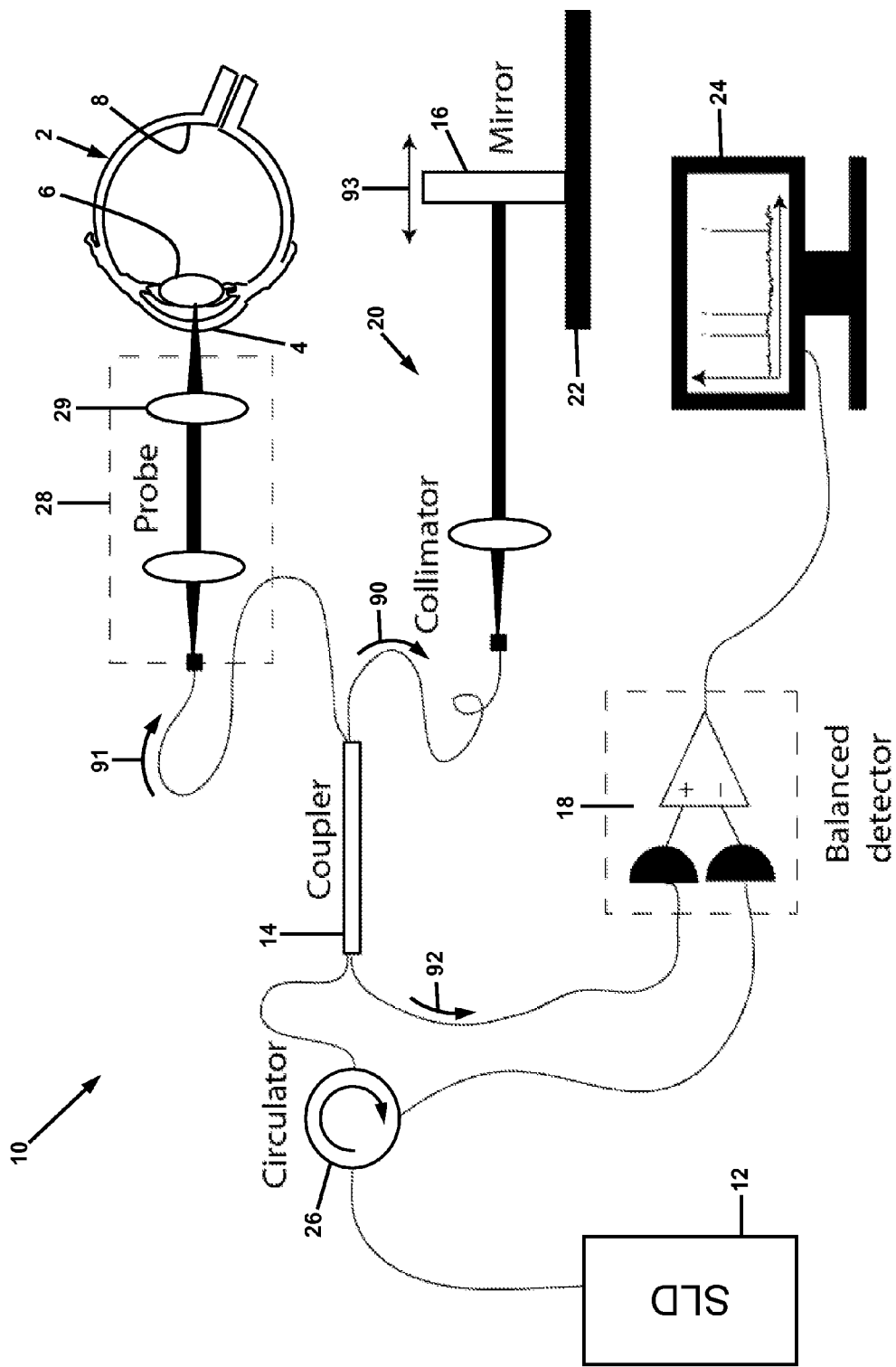
FIG. 1 is a schematic diagram of an eye measurement system that uses time domain interferometry.

The present invention will be described in connection with a preferred embodiment, however, it will be understood that there is no intent to limit the invention to the embodiment described. On the contrary, the invention is defined and limited only by the claims.

DETAILED DESCRIPTION

For a general understanding of the present invention, reference is made to the drawings. In the drawings, like reference numerals have been used throughout to designate identical or equivalent elements. In describing the present invention, a variety of terms are used in the description.

As used herein, the terms "measurement system" and "measurement apparatus" are used interchangeably and are meant to indicate an assembly of components that can be used for making a measurement.

As used herein, the term "low coherence light source" means a light source having a coherence length which is short enough to permit resolution of the structures that are to be measured. Preferably, this is equal or less than the thickness of the thinnest anatomical structures to be measured. A coherence length of less than 50 microns is often sufficient for this purpose.

FIG. 1 is a schematic diagram of an eye measurement system that uses time domain interferometry to perform axial measurements of an eye. The system is based upon the principles of the Michelson interferometer. System 10 is comprised of a low coherence light source 12, a beam splitter 14, a movable mirror 16, a detector 18, and various optical fibers for guiding light between the components.

In operation, light emitted from source 12 is split into two beams by the beam splitter 14, which may be a fiber optic coupler. One of the two beams is directed toward the movable mirror 16 as indicated by arrow 90 and forms a reference arm 20 of the interferometer. The other beam is directed as indicated by arrow 91 towards an object to be measured, in this case, an eye 2 of a human patient. The eye is comprised of a cornea 4, an intraocular lens 6, and a retina 8, which include reflective interfaces. Some of the light directed onto and into the eye 2 is thus reflected back. This reflected light from the various interfaces within the eye and the light reflected by the mirror 16 are then recombined and directed to the detector 18 as indicated by arrow 92.

An interference signal occurs when the optical path length of the reference arm 20 is equal to the optical distance to a reflective surface in the eye 2 to within the coherence length of the light from source 12. When the reference mirror 16 is moved by a motorized linear stage 22 or other suitable means as indicated by arrow 93, interference occurs between the reflected light from the mirror and the reflected light from the various interfaces of the eye 2 due to changes in the length of the reference arm 20. The system 10 is further comprised of a computer 24 in communication with the detector 18. The computer 24 receives a signal from the detector 18 during the scanning movement of the mirror 16, and uses algorithms to calculate the complete dimensional information of the layered structure of the eye, including the total axial length.

The system 10 further includes a circulator 26 and may also include a probe 28 that may include at least one lens 29 for focusing the light beam along the axis of the eye 2. The low coherence light source 12 may be a super luminescent diode (SLED), such as an Exalos EXS8510-1411. The SLED should emit at wavelengths where the eye is sufficiently transparent and the patient does not experience discomfort. A preferred range of wavelengths is 600 nm to 1200 nm.

The applicant has made a working example of system 10 suitable for time domain interferometry, in which the total travel distance of the mirror 16 is 50 millimeters (mm), the travel is performed at constant velocity, and the duration of travel between the maximum forward and rearward positions is about one second, thereby providing a measurement rate of 1 Hz. In this exemplary system, the power of the light incident on the retina 8 of the eye 2 is approximately 350 microwatts, which is well below the generally accepted safe limit (as specified by ANSI Standard Z136.1-2000). Using the system 10 of FIG. 1, a clinical study on several human subjects has been conducted. Measured axial lengths of the subject's eyes ranged from 23.4 mm to 28.06 mm with standard deviations less than 0.03 mm.

Figure 2:
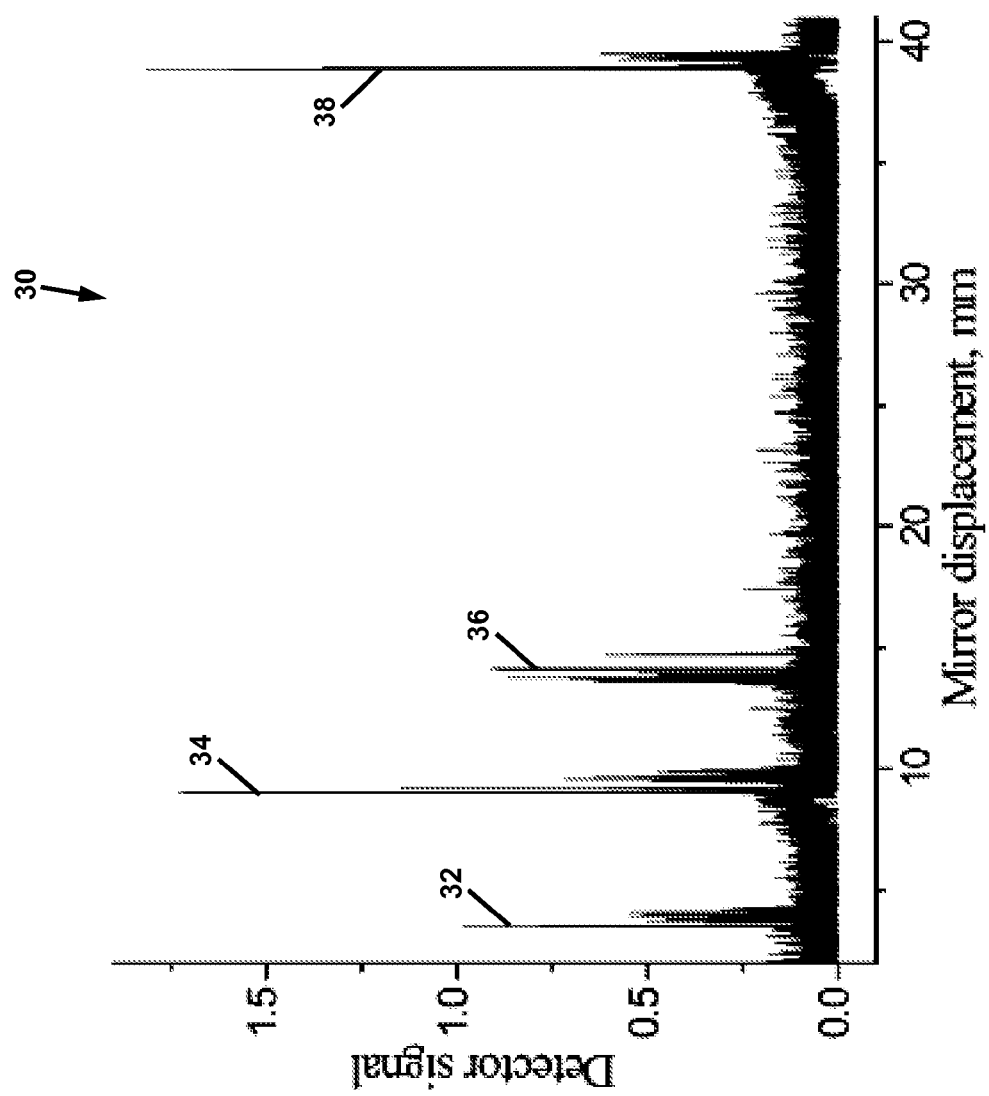
FIG. 2 is an interferogram of a human eye obtained by the use of the system of FIG. 1.

FIG. 2 shows a typical interferogram acquired for an in-vivo human eye during a single scan of the mirror 16. Each peak in the interferogram 30 corresponds to a reflective interface formed by the cornea, crystalline lens and retina. The distances between the peaks correspond to the optical distances between the respective interfaces, which allows to measure corneal thickness, lens thickness and anterior chamber depth simultaneously with the total axial length. Referring to FIG. 2 from left to right, the first group 32 of peaks corresponds to the cornea, the second and third groups 34 and 36 correspond to the crystalline lens, and the fourth group 38 corresponds to the retina.

Although system 10 can provide precise measurements of the axial length of an eye, it is not optimal because the measurement rate of about 1 Hz is lower than what is desired. The system is limited by the rate at which the mirror 16 can be scanned from its maximum forward position to its maximum rearward position.

Figure 3:
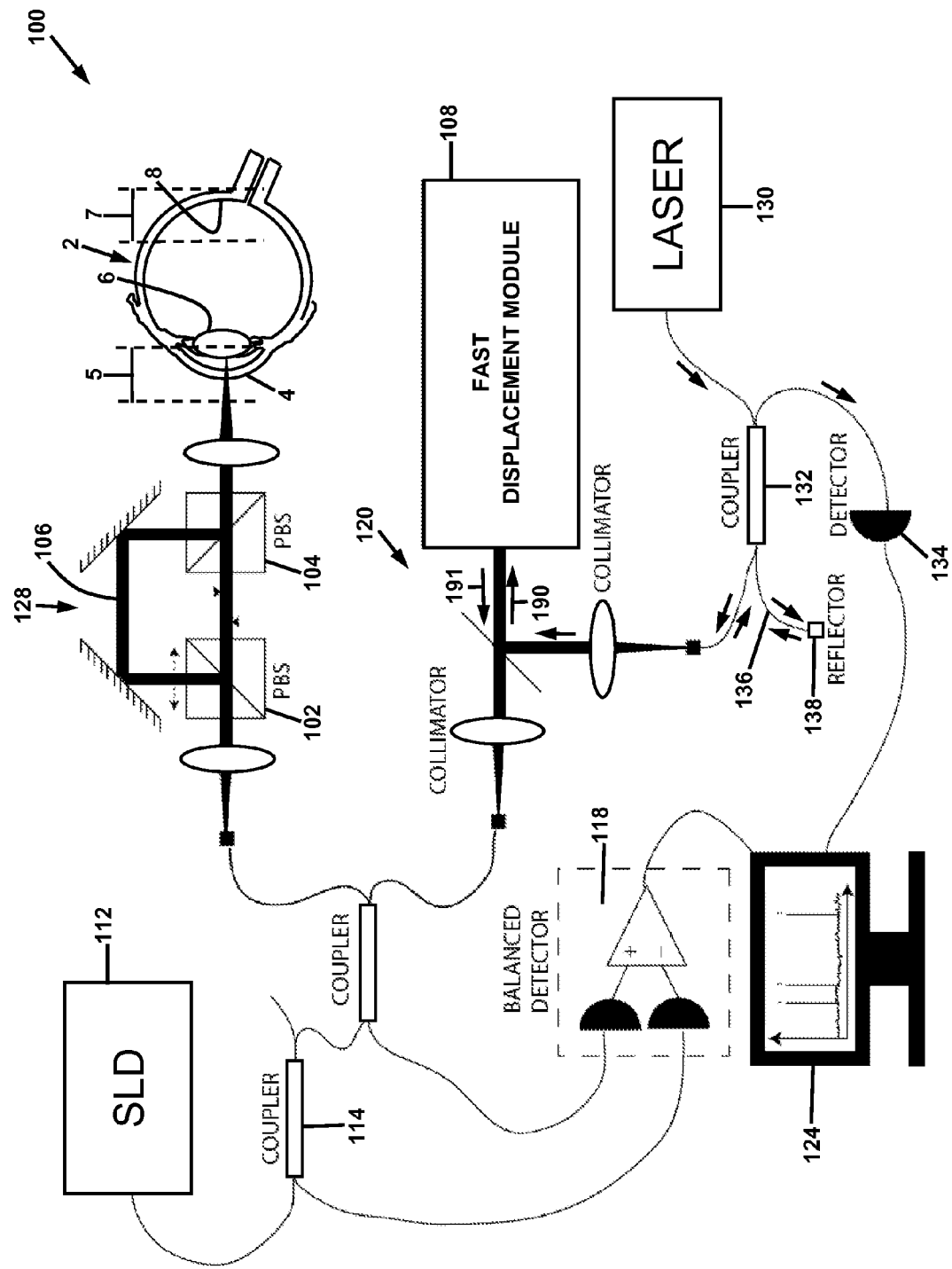
FIG. 3 is a schematic diagram of an eye measurement system for performing fast axial eye measurements.

To address this problem, the applicant has invented a measurement system for performing fast axial eye measurements. A schematic diagram of the applicant's system 100 is shown in FIG. 3. The system 100 is comprised of a low coherence light source 112, a beam splitter 114, a detector 118, a computer 124, and various optical fibers for guiding light between the components, similar to the corresponding components of system 10 of FIG. 1. However, there are three main components that differ from the configuration of the system 10.

First, the optical probe 128 of system 100 is comprised of a first polarizing beam splitter 102 and a second polarizing beam splitter 104. The low coherence light in the probe 128 is split into two orthogonal polarizations. One of the polarized beams 106 travels through an offset that is substantially equal to the average length of the human eye. In that manner, a much smaller scanning range of the reference arm 120 of the system 100 is required to probe the locations of the cornea 4 and the retina 8. A substantial portion of the eye 2 between the intraocular lens 6 and the retina 8 does not contain useful information and therefore does not need to be probed. The configuration of the system 100 allows skipping this empty vitreous space, i.e. no measurements are performed in it. Accordingly, the scanning range of the reference arm 120 is much shorter than the system 10 of FIG. 1. Additionally, using the polarization split instead of a simple power split also helps to preserve the sensitivity of the system by minimizing the light loss therefrom.

Second, the reduced requirement for the scanning range of the reference arm 120 enables the use of several alternative displacement techniques (other than the motorized linear stage 22 of FIG. 1), which can operate at faster scanning rates. Referring again to FIG. 3, a "fast displacement module" 108 is provided that includes means for rapidly varying the path length of the reference arm 120. Two examples of such means will be described subsequently in this specification with reference to FIGS. 4A and 4B.

Third, in order to precisely measure the scanning distance of the displacement module 108, system 100 is further comprised of a laser 130. Light from laser 130 is co-propagated along the path of the low-coherence light as indicated by arrows 190 and 191. The laser light reflected back from the displacement module 108 is then guided back through a coupler 132 and into a separate interferometer 134, the reference arm of which is formed by an optical fiber 136 that is connected to reflector 138. The computer 124 receives a signal from interferometer 134, which enables monitoring of the changes of the path length of reference arm 120 with a sub-micrometer precision. The wavelength of the laser should be different from the spectrum of the low coherence light source 112. In one embodiment, the low coherence light source may be an SLED having a spectrum centered at about 850 nm, while the laser may be a helium neon laser that emits a beam of 633 nanometers.

It is generally known that the axial length of human eyes varies within a 6 mm range for 98% of the general population. See, Stenstrom S., *American Journal of Optometry*, Vol. 25, pp. 340-350 (1948). Assuming an average refractive index of 1.35 of the eye tissues, lens and fluids, the required total minimum change in the reference beam path length is 8.1 mm. In order to remove the edge effects and to avoid possible overlapping between the corneal and retinal signals, the total motion range of the reference beam path length produced by the fast displacement module 108 should be approximately 10 mm.

In order to attain the desired 15 Hz measurement rate for a 10 mm path length change, the required displacement speed is 150 mm/sec, which is 3 times faster than the speed used in the system 10 of FIG. 1. It is noted that higher motion speed requires broadband detection electronics, and therefore results in higher electronic noise and reduced sensitivity. To maintain sufficient sensitivity, it is preferable that the amount of light incident in the eye be increased to 700 microwatts.

Figure 4A:
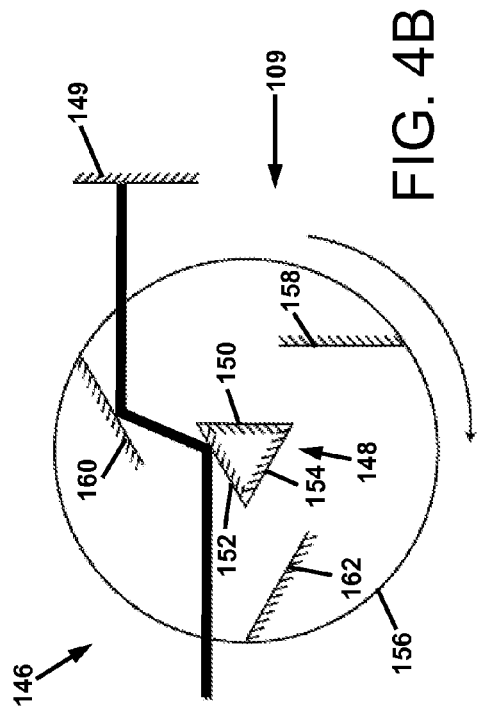
FIG. 4A is a schematic diagram of a displacement module of the system of FIG. 3 that includes a rotating cube.

A variety of suitable means for rapidly varying the path length of the reference arm 120 may be provided in fast displacement module 108, which achieve the 10 mm displacement or path length change at the required 15 Hz rate. These can include fiber stretchers. The applicant has determined that rotation-based devices are likely to be more cost effective. Two exemplary devices for the fast displacement module 108 are depicted in FIGS. 4A and 4B. FIG. 4A shows a fast displacement module that operates by refraction. FIG. 4B shows a fast displacement module that operates by reflection.

Figure 4C:
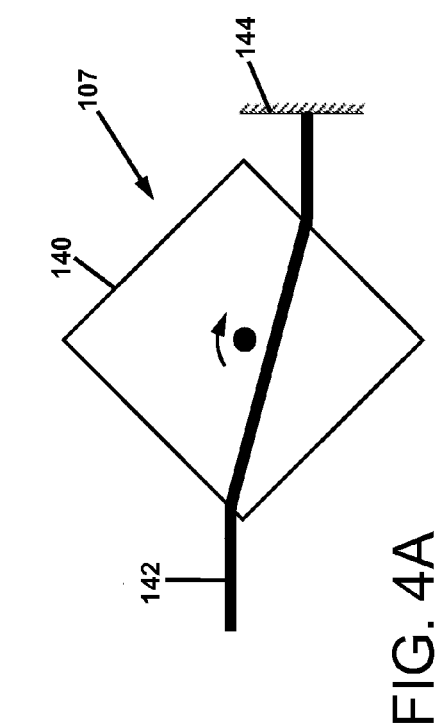
FIG. 4C is a plot of the dependence of path length through the module on cube rotation angle for the fast displacement module of FIG. 4A.
Figure 4B:
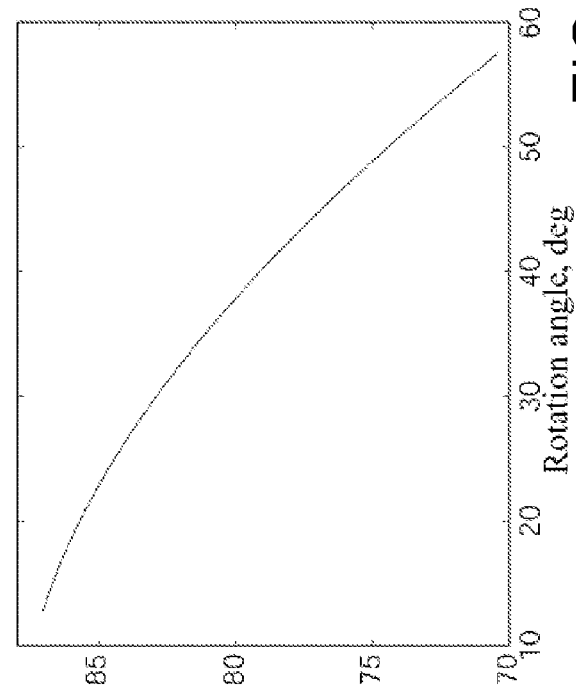
FIG. 4B is a schematic diagram of a displacement module of the system of FIG. 3 that includes a rotating mirror assembly.

FIG. 4A is a schematic diagram of a fast displacement module 107 comprised of a rotating cube 140; and FIG. 4C is a plot of the dependence of path length through the module 107 on cube rotation angle for one exemplary cube that may be used in the module of FIG. 4A. Referring to FIG. 4A, as the cube 140 rotates, the incident beam 142 is refracted by the cube 140, and is then reflected back by a stationary plane mirror 144. When the cube rotates around its axis, the total distance that the light beam 142 travels increases while it first propagates inwardly through the cube 140 toward the mirror 144, and then back outwardly through the cube 140. Because the refractive index of the glass is larger than the refractive index of air, the total path length also increases. The calculated total path length change through the reference arm 120 versus the rotation angle is shown in FIG. 4C. By way of example, and not limitation, a total of 18 mm of path length change is possible with a 1 inch cube. Referring to FIG. 4B, it can be seen that as a 1 inch cube 140 rotates through an angular displacement of about 70 degrees, the total path length through the reference arm 120 increases from about 75 mm to about 93 mm. This is a result of the change in path length of 18 mm through the cube 140 during that 70 degree rotation. It is noted that the practical range may be less due to the nonlinearity in the path length curve. Additionally, it is noted that each side of the cube may be used for path length modulation; thus the rotation frequency of the cube may be limited to only about 4 Hz, which gives a measurement rate of 16 Hz.

Figure 4D:
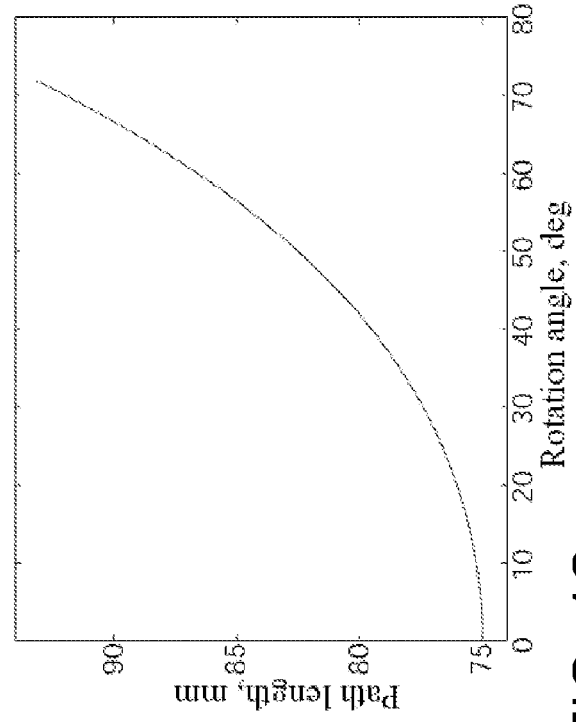
FIG. 4D is a plot of the dependence of path length through the module on mirror assembly rotation angle for the fast displacement module of FIG. 4B.

FIG. 4B is a schematic diagram of an alternative fast displacement module 109 comprised of a rotating mirror assembly 146; and FIG. 4D is a plot of the dependence of path length through the module 109 on mirror assembly rotation angle for one exemplary mirror assembly that may be used in the module 109 of FIG. 4B. The mirror assembly 146 is comprised of pairs of parallel rotating mirrors. In the embodiment depicted in FIG. 4B, the mirror assembly 146 includes three pairs of parallel rotating mirrors. The mirror assembly 146 has a triangle mirror 148 having mirror sides 150, 152, and 154. The triangle mirror 148 is disposed on a rotating disc 156 and centered at the rotational axis thereof. The mirror assembly 146 is further comprised of mirrors 158, 160, and 162, which are joined to the rotating disc 156, and which are parallel respectively to mirror sides 150, 152, and 154 of triangle mirror 148. Thus three pairs of parallel mirrors are formed by triangle mirror 148 and mirrors 158, 160, and 162.

Displacement module 109 is further comprised of mirror 149 which terminates the path of the reference arm 120.

The fast displacement module 109 is more advantageous compared to the displacement module 107 of FIG. 4A, since, as a reflective unit, it does not require path calibration. The co-propagating beam from laser 130 can be used to determine the path length changes directly. The calculated total path length change through the reference arm 120 versus the rotation angle for the displacement module 109 is shown in FIG. 4D. It can be seen that there is a near-linear dependence on the rotation angle, which is advantageous in maintaining equal sensitivity along the scan of path length. By way of example, and not limitation, a total displacement of 16 mm for a 3 inch diameter rotating disc may be attained. Referring to FIG. 4D, it can be seen that as the 3 inch diameter mirror assembly 146 rotates through an angular displacement of about 45 degrees, the total path length through the reference arm 120 increases from about 71 mm to about 87 mm. This is a result of the change in path length of 16 mm through the mirror assembly 146 during that 45 degree rotation. Since the three identical reflecting paths may be used for path length modulation, a 15 Hz measurement rate may be achieved by rotating the disc 156 at 5 Hz.

Referring again to FIG. 3, when the fast displacement module 108 completes a single scan, two 10 millimeter regions of the eye 2 are simultaneously probed. This is a result of having provided the optical probe 128 with the first polarizing beam splitter 102 and the second polarizing beam splitter 104. Two polarized beams are produced and directed into the eye, with the beams differing in path length by the average length of the human eye. The two regions of the eye 2 that are probed are the cornea region 5 and the retina 7.

Thus the data from a scan of the eye 2 contains two sets of peaks corresponding to the cornea and the retina. The distance between the regions that are scanned by the system 100 is controlled by the offset between the two paths traveled by the two orthogonal polarizations. The offset is deliberately chosen to be the average axial length of a human eye so that the scanned regions are the cornea region 5 and the retina region 7. The overall configuration of the system 100 of FIG. 3 enables this distance to be measured with the desired high precision and high speed.

It is important note that in a further embodiment wherein the scanning range of the displacement module 109 is increased further to, for example, 20 mm, all reflecting surfaces within the eye can be detected. In this embodiment, the anterior chamber depth and the lens thickness distance can be measured in addition to the corneal thickness and the total axial length of the eye.

It is, therefore, apparent that there has been provided, in accordance with the present invention, an apparatus for measuring the axial length of a human eye. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. A method for measuring the axial length of a human eye, the method comprising the steps of:
providing a low coherence light source, a laser, a beam splitter, a fast displacement module, and a first and second interferometer;
rapidly varying, by the fast displacement module, the path length within a reference arm of the first interferometer;

co-propagating a laser beam from the laser with light from the low coherence light source into the displacement module; and monitoring, by the second interferometer, the path length of the laser beam.

2. A method for measuring the axial length of a human eye, the method comprising the steps of:

providing a low coherence light source, a laser, a beam splitter, a fast displacement module, a first and second interferometer, and an optical probe, wherein the optical probe is comprised of a first polarizing beam splitter and a second polarizing beam splitter positioned to provide two polarized beams having path lengths that differ by an offset that is substantially equal to the average length of the human eye wherein the first and second polarizing beam splitters are located between the low coherence light source and the eye;

rapidly varying, by the fast displacement module, the path length within a reference arm of the first interferometer;

co-propagating a laser beam from the laser with light from the low coherence light source into the displacement module; and monitoring, by the second interferometer, the path length of the laser beam.

3. A method for measuring the axial length between an outer surface and an inner surface of a human eye, the method comprising:

directing a first portion of low coherence light from a source through an optical probe and into the eye;

reflecting a first part of the first portion of low coherence light off the outer surface of the eye back through the optical probe to a first detector;

reflecting a second part of the first portion of low coherence light off the inner surface of the eye back through the optical probe to the first detector;

co-propagating laser light and a second portion of the low coherence light through the reference arm of a first interferometer, while operating a fast displacement module in the reference arm to vary the path length within the reference arm;

detecting a first interference signal when the path length through the reference arm is equal to the path length through the optical probe to the outer surface of the eye, and detecting a second interference signal when the path length through the reference arm is equal to the path length through the optical probe to the inner surface of the eye;

measuring the path length of the laser beam through the reference arm with a second interferometer; and calculating the length between the outer surface and the inner surface of the eye based upon the path lengths through the reference arm when the first interference signal occurred and when the second interference signal occurred.

4. The method of claim 3, wherein the optical probe is comprised of a first polarizing beam splitter and a second polarizing beam splitter positioned to provide two polarized beams having path lengths that differ by an offset that is substantially equal to the axial length of the eye.

5. The method of claim 4, wherein the outer surface of the eye is the corneal surface, the inner surface of the eye is the retinal surface, the eye is further comprised of a lens comprising a front surface and a rear surface, and the method further comprises:

detecting a third interference signal when the path length through the reference arm of the first interferometer is equal to the path length through the optical probe to the front lens surface, and detecting a fourth interference signal when the path length through the reference arm of the first interferometer is equal to the path length through the optical probe to the rear lens surface;

calculating the length between the front lens surface and one of the outer surface and the inner surface of the eye; and calculating the length between the rear lens surface and one of the outer surface and the inner surface of the eye.

* * * * *